United States Patent [19]

Miyazaki et al.

[11] Patent Number: 5,170,063

[45] Date of Patent: Dec. 8, 1992

[54] INSPECTION DEVICE FOR DETECTING DEFECTS IN A PERIODIC PATTERN ON A SEMICONDUCTOR WAFER

[75] Inventors: Yoko Miyazaki; Hitoshi Tanaka; Nobuyuki Kosaka; Toshimasa Tomoda, all of Amagasaki, Japan

[73] Assignee: Mitsubishi Denki Kabushiki Kaisha, Tokyo, Japan

[21] Appl. No.: 661,140

[22] Filed: Feb. 27, 1991

[30] Foreign Application Priority Data

Feb. 28, 1990 [JP] Japan .................................. 2-48156

[51] Int. Cl.$^5$ ............................................. G01B 9/021
[52] U.S. Cl. .................................... 250/572; 356/347; 359/564
[58] Field of Search ................. 250/572, 562; 359/10, 359/11, 561, 564; 356/349, 347

[56] References Cited

U.S. PATENT DOCUMENTS 4,674,824  6/1987  Goodman et al. ................. 350/3.64
4,857,425  8/1989  Phillips .................................. 354/10
4,929,081  5/1990  Yamamoto et al. ................. 356/347

OTHER PUBLICATIONS

D. L. Cavan et al., "Patterned Wafer Inspection Using Laser Holography And Spatial Frequency Filtering", Journal of Vacuum Science Technology B6 (6), Nov./Dec. 1988, pp. 1934–1939.

Primary Examiner—Janice A. Howell
Assistant Examiner—Richard Hanig
Attorney, Agent, or Firm—Leydig, Voit & Mayer

[57] ABSTRACT

An inspection device for detecting defects in a periodic pattern on a semiconductor wafer includes a laser oscillator. In the exposure process, light emitted from the laser oscillator is divided into a subject beam and a reference beam. The subject beam is guided to a semiconductor wafer having a periodic pattern thereon by mirrors and a beam expander. The light scattered from the specimen is collected by a lens on a photographic plate. The reference beam is guided to the photographic plate via a second beam expander and another mirror. The intensity of the reference beam is adjusted to a level at which the reference beams interferes on the photographic plate with the light scattered from defects in the periodic pattern and collected by the lens. Thus, a hologram of the defects in the pattern is recorded on the photographic plate. After development, the photographic plate is returned to its original position and used to form a holographic image of the defects with a transmitted regeneration light beam.

5 Claims, 6 Drawing Sheets

INSPECTION DEVICE FOR DETECTING DEFECTS IN A PERIODIC PATTERN ON A SEMICONDUCTOR WAFER

BACKGROUND OF THE INVENTION

This invention relates to pattern defect inspection devices for detecting defects in fine repetitive (i.e., periodic) patterns formed, for example, on semiconductor integrated circuits or TFT liquid crystal planar display elements.

FIGS. 1 through 3 schematically show the optical configuration of a typical pattern defect inspection device, which is disclosed, for example, in a technical journal, "Electronics", p. 74, March 1987. FIGS. 1 and 2 show the exposure processes of the Fourier transform filter and the hologram, respectively, while FIG. 3 shows the defect inspection process by which a holographic image (real image) of the defects is formed and examined.

The exposure of the Fourier transform filter is effected as shown in FIG. 1. The light 31 emitted from the laser oscillator 1 and reflected by the reflection mirror 2, beam splitter 3, reflection mirror 4, and reflection mirror 5, is expanded via the beam expander 6. The expanded parallel beam from the beam expander 6 illuminates a specimen (semiconductor wafer) 9 via the reflection mirror 7 and half reflection mirror 8. At this time, a wafer having a normal or proper periodic pattern without any defects is utilized as the specimen 9. (Practically, however, it suffices to use a wafer with only a small number of defects.) The light reflected and diffracted from the repetitive pattern on the specimen (semiconductor wafer) 9 is collected by the lens 10 via the half reflection mirror 8, and forms a spatial frequency pattern (Fourier transform pattern) of the pattern on the specimen 9 on the first photographic plate 11 positioned at the back focal plane of the lens 10. The Fourier transform (spatial frequency) pattern of the pattern on the specimen (semiconductor wafer) 9 without any defects is thus recorded on the first photographic plate 11. The first photographic plate 11 is then developed by a well-known chemical process and is returned to the original position in order to serve as the spatial frequency filter in the subsequent processes described hereinbelow.

Thereafter, the specimen (semiconductor wafer) 9 is replaced by a specimen (semiconductor wafer) which is to be actually inspected and which may have many defects, and the exposure of the second photographic plate 12 is effected as shown in FIG. 2 in order to obtain the hologram of the defects of the pattern on the specimen (semiconductor wafer) 9. The light emitted from the laser oscillator 1 and reflected by the reflection mirror 2 is split into subject beam 31 and reference beam 32 via the beam splitter 3. The subject beam 31 illuminates the specimen (semiconductor wafer) 9 via the same optical path as in FIG. 1. Further, the light reflected and diffracted from the specimen (semiconductor wafer) 9 reaches the first photographic plate 11 via the same optical path as in FIG. 1. Thus, the information corresponding to the normal periodic pattern (i.e., the pattern without defects) on the specimen (semiconductor wafer) 9 is removed from the light passing through the first photographic plate 11, and hence only the information which corresponds to the defects of the pattern on the specimen (semiconductor wafer) 9 reaches the second photographic plate 12. On the other hand, the reference beam 32, reflected via the reflection mirror 13 and the reflection mirror 14, expanded via the beam expander 15, and reflected again via the reflection mirror 16 and the reflection mirror 17, illuminates the second photographic plate 12. Thus, the defect information from the specimen (semiconductor wafer) 9 is recorded on the second photographic plate 12 in the form of a hologram. The second photographic plate 12 is then developed by a well known chemical process and is returned to the original position to serve as the hologram of the defects of the pattern on the specimen (semiconductor wafer) 9.

The inspection of the defects of the specimen (semiconductor wafer) 9 is effected as shown in FIG. 3. The regeneration beam 33 emitted from the laser oscillator 1 is reflected by the reflection mirror 2, transmitted through the beam splitter 3, reflected again by the reflection mirror 13 and reflection mirror 14, and expanded into a parallel expanded beam via the beam expander 15. The expanded beam from the beam expander 15 passing at the side of the reflection mirror 16 moved out of the optical path is reflected by the reflection mirror 18 to illuminate the second photographic plate as the regeneration beam 33 proceeding in the direction opposite to that of the reference beam 32 of FIG. 2 reflected by the reflection mirror 17. Thus, the light passing through the hologram of the pattern defects recorded in the second photographic plate 12 forms, via the first photographic plate, lens 10, and half reflection mirror 8, the holographic image (real defect image) 91 at the position at which the specimen (semiconductor wafer) 9 had been positioned. The optical detector 19 detects the holographic image (real defect image) 91 as the defect information of the pattern on the specimen (semiconductor wafer) 9.

The above conventional pattern defect inspection device, however, has the following disadvantage. The device is in need of the first photographic plate serving as the spatial frequency filter and the second photographic plate serving as the hologram of the defects of the pattern on the specimen. Thus, the pattern defect inspection device is complicated in organization and hence is large is size.

SUMMARY OF INVENTION

It is therefore an object of this invention to provide a pattern defect inspection device which is simple in optical configuration and hence is small in size. More particularly, this invention aims at providing a pattern defect inspection device which eliminates the need for the spatial frequency filter for the normal periodic pattern.

The above objects are accomplished in accordance with the principle of this invention by a pattern defect inspection device which comprises: a coherent light source (such as a laser oscillator) for emitting a coherent light beam; a beam splitter means for dividing said coherent light beam emitted from the coherent light source into a subject beam and a reference beam; a first optical path means for guiding said subject beam onto said object having a periodic pattern formed thereon; a collecting lens for collecting light scattered from said surface of said object; a photographic plate positioned at a back focal plane of said lens; a second optical path means for guiding said reference beam to said photographic plate in a forward direction, wherein an intensity of said reference beam is adjusted to a level at which said reference beam interferes on said photographic plate solely with a weaker part of light scattered from said object and collected by said lens, said weaker part corresponding to a defect of said pattern, a hologram of said defect thereby being recorded in said photographic plate; a third optical path means for guiding a coherent regeneration light beam generated by said coherent light source to said second photographic plate in a reverse direction opposite to said forward direction, said second photographic plate serving as a hologram, a holographic image of said defect thereby being formed via said regeneration light beam passing via said photographic plate and said lens; and an optical detector for detecting said defect from said holographic image.

BRIEF DESCRIPTION OF THE DRAWINGS

The features which are believed to be characteristic of this invention are set forth in the appended claims. This invention itself, however, may best be understood from the detailed description of the preferred embodiments, taken in connection with the accompanying drawings, in which:

FIGS. 1 through 3 are schematic views showing the optical configuration of a conventional pattern defect inspection device, wherein FIGS. 1 and 2 show configurations in the exposure process while FIG. 3 shows the configurations in the inspection process;

FIGS. 4 and 5 are schematic views showing the optical configuration of a pattern defect inspection device according to this invention, wherein FIG. 4 shows the configuration in the exposure process while FIG. 5 shows the configuration in the defect inspection process.

In the drawings, like reference numerals represent like or corresponding parts.

DETAILED DESCRIPTION OF THE PREFERRED EMBODIMENTS

Figure 1:
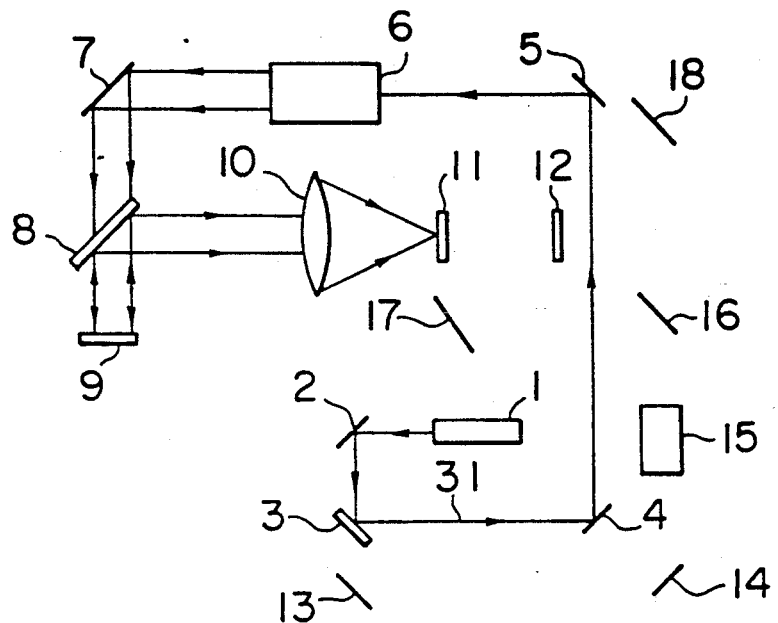
Figure 2:
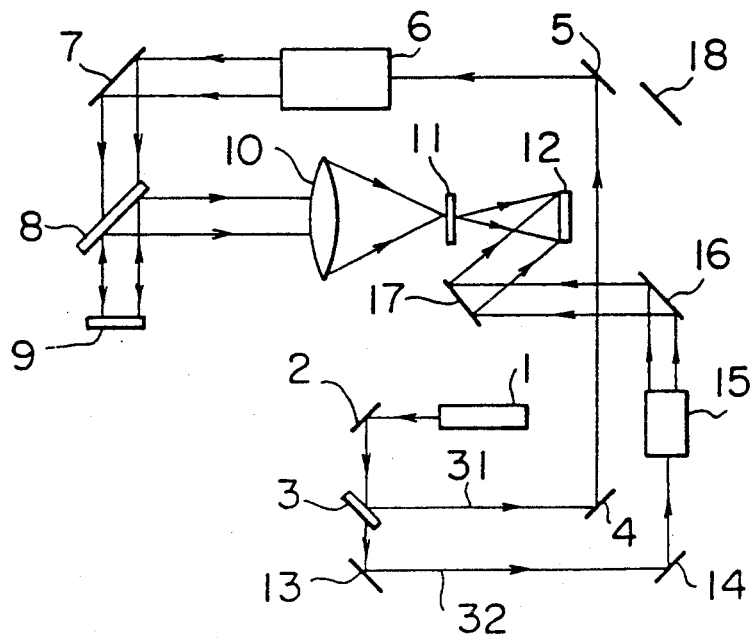
Figure 3:
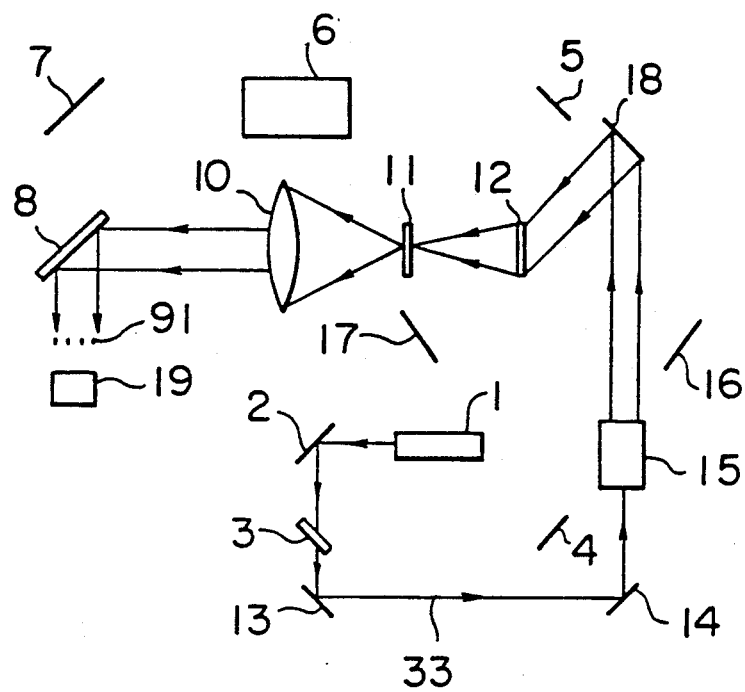
Figure 4:
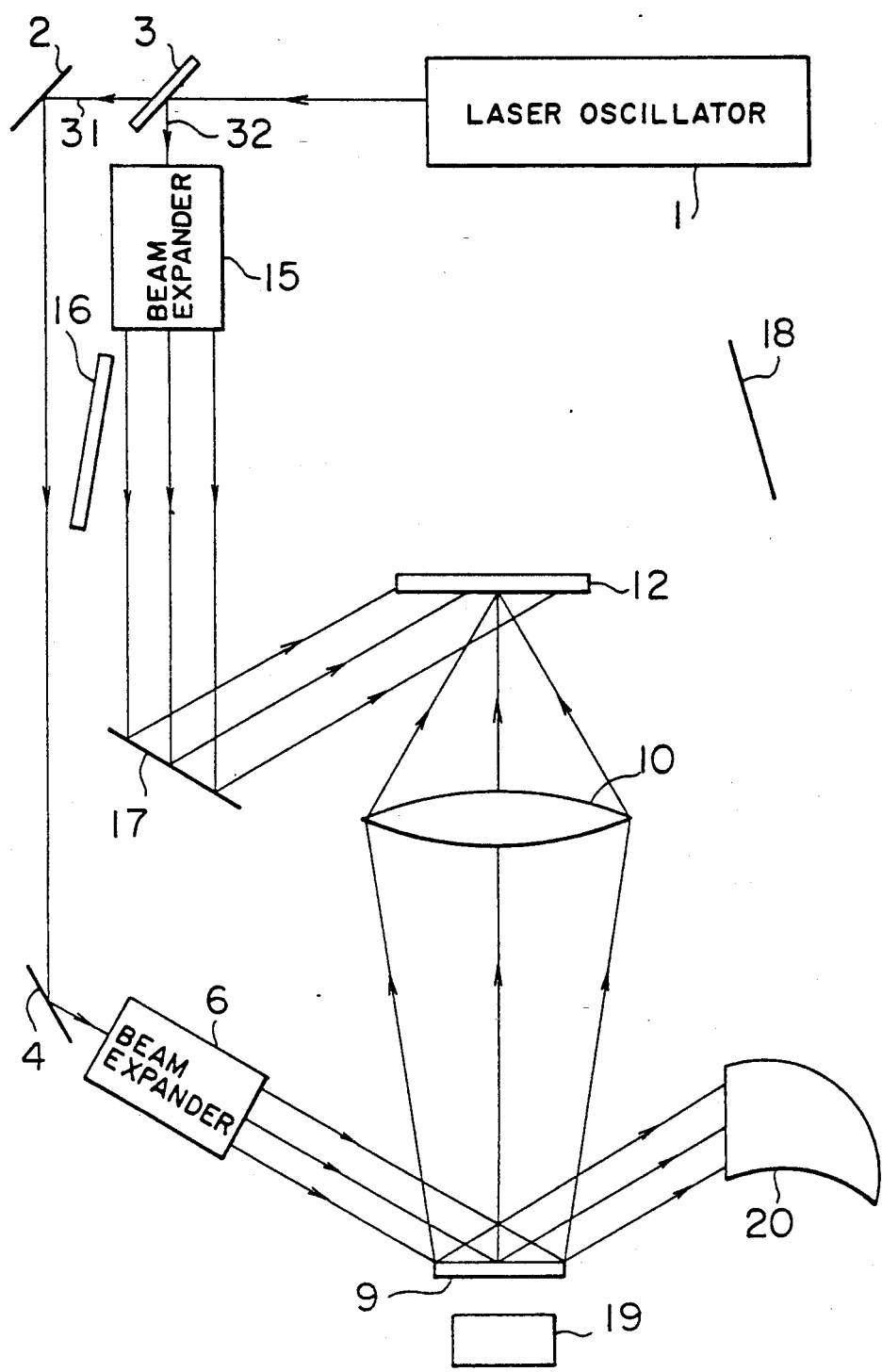
Figure 5:
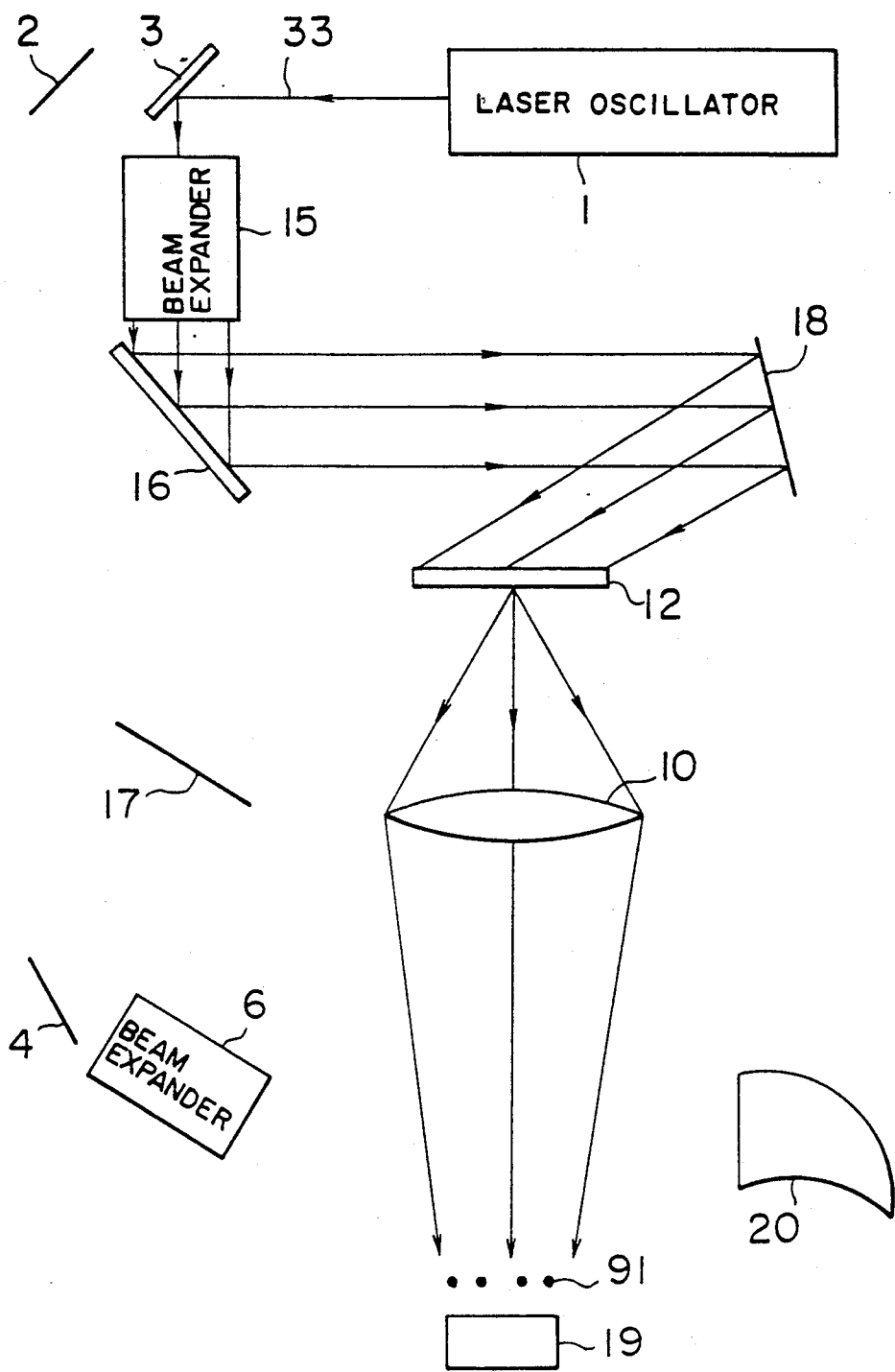

Referring first to FIGS. 4 and 5, a first embodiment according to this invention is described. It is noted that reference numeral 20 designates a light trap for trapping the stray light. Other parts are designated by the same reference numerals as in FIGS. 1 through 3.

The exposure of photographic plate 12 for obtaining the hologram of the defects of the pattern is effected as shown in FIG. 4. The light emitted from the laser oscillator 1 is divided by the beam splitter 3 into the subject beam 31 and the reference beam 32. The subject beam 31 is guided via the reflection mirror 2 and the reflection mirror 4 into the beam expander 6. The expanded parallel beam obtained by the beam expander 6 obliquely illuminates (at an arbitrary angle, but preferably at 45 degrees) the whole surface of the specimen (semiconductor wafer) 9. The light specularly reflected from the surface of the specimen (semiconductor wafer) 9 is trapped by the light trap 20 and thus is removed from the optical path for forming the hologram. The light scattered from the specimen (semiconductor wafer) 9 is collected by the lens 10 and reaches the photographic plate 12 positioned at the back focal plane of the lens 10. On the other hand, the reference beam 32 guided into the beam expander 15 via the beam splitter 3 is expanded by the beam expander 15 into a parallel beam, which is guided via the reflection mirror 17 to the photographic plate 12 to illuminate the whole surface thereof.

The pattern on the surface of specimen (semiconductor wafer) 9 may have defects. Thus, the light is scattered not only by the normal or proper repetitive pattern but also by the defects thereof. The light scattered from the defects is weaker in intensity than the light scattered from the normal repetitive (i.e., periodic) pattern. Thus, the intensity of the reference beam 32 and the length of the optical path of the reference beam 32 are adjusted to values at which the reference beam 32 interferes selectively with the weaker part of the light scattered from the surface of the specimen (semiconductor wafer) 9 and is guided onto the photographic plate 12. As a result, the defects on the specimen (semiconductor wafer) 9 are recorded on the photographic plate 12 as a hologram. On the other hand, the light scattered from the normal periodic pattern is collected into a light beam of strong intensity, such that even when it interferes with the reference beam 32, it is not recorded as interference fringes but as a mere Fourier transform pattern and hence does not form a hologram. Thus, the normal periodic pattern is not reproduced in the subsequent inspection procedure. The exposure of the photographic plate 12 is thus completed.

The photographic plate 12 on which the hologram of the defects of the specimen (semiconductor wafer) 9 has been recorded is developed by a well-known chemical process and then is returned to the original position. Thereafter, the inspection of the defects on the specimen (semiconductor wafer) 9 is effected as shown in FIG. 5. Namely, the regeneration beam 33 emitted from the laser oscillator 1 is guided to the beam expander 15 via the beam splitter 3, and the expanded parallel beam from the beam expander 15 illuminates the photographic plate 12 via the reflection mirror 16 (which is now positioned obliquely across the optical path of the expanded beam of the beam expander 15) and the reflection mirror 18. The expanded beam from the mirror 18 illuminates the photographic plate 12 from a direction opposite to the direction of illumination of the reference beam 32 of FIG. 4 reflected from the reflection mirror 17. Thus, the light passing through the hologram 12 forms, via the lens 10, a holographic image (real defect image) 91 at the position at which the specimen (semiconductor wafer) 9 was positioned in the exposure process. The optical detector 19 detects the positions and the magnitudes of the defects from the holographic image (real defect image) 91.

Figure 6:
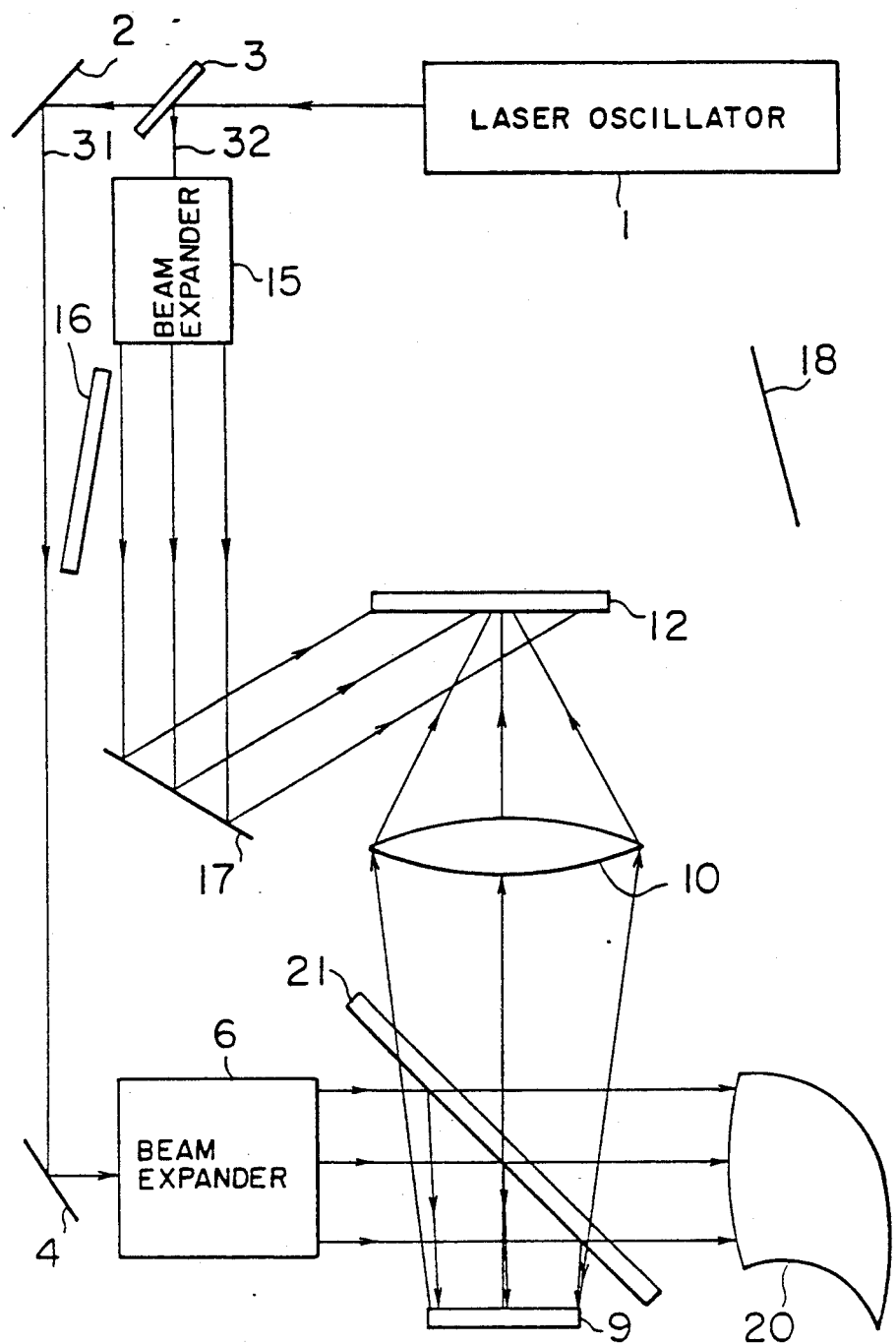
FIGS. 6 and 7 are views similar to that of FIG. 4, but showing the optical configurations of a second and a third embodiment according to this invention.

FIG. 6 shows the optical configuration of another embodiment according to this invention in the exposure process, by which the subject beam 31 expanded by the beam expander 6 illuminates the specimen (semiconductor wafer) 9 via a half reflection mirror 21, such that the light reflected from the half reflection mirror 21 is incident on the specimen (semiconductor wafer) 9 at a right angle to the surface thereof. On the other hand, the light which transmitted through the half reflection mirror 21 is collected by the light trap 20 and thus is removed from the optical path for the hologram. The light reflected regularly from the surface of the specimen (semiconductor wafer) 9 is converged by the lens 10 into a single point on the photographic plate 12, which point has a strong intensity and hence does not form a hologram on the photographic plate with the reference beam 32 expanded via the beam expander 15 and illuminating the photographic plate 12 in the forward direction via the reflection mirror 17. Thus, just as in the case of the above embodiment, the spatial frequency pattern or the hologram of the defects of the pattern on the specimen (semiconductor wafer) 9 is recorded on the photographic plate. In the defects inspection process, the reflection mirror 16 is positioned obliquely across the optical path of the expanded beam from the beam expander 15 such that the regeneration beam 33 (not shown) expanded by the beam expander 15 and reflected by the reflection mirror 16 and reflection mirror 18 illuminates the photographic plate 12 from the reverse direction. Further, the half reflection mirror 21 and the specimen (semiconductor wafer) 9 are removed and an optical detector (not shown) is positioned to observe the holographic image of the defects. Alternatively, the half reflection mirror 21 is retained at its position and the optical detector (not shown) is positioned at the focus of the lens 10 on the optical path of the light reflected by the half reflection mirror 21.

Figure 7:
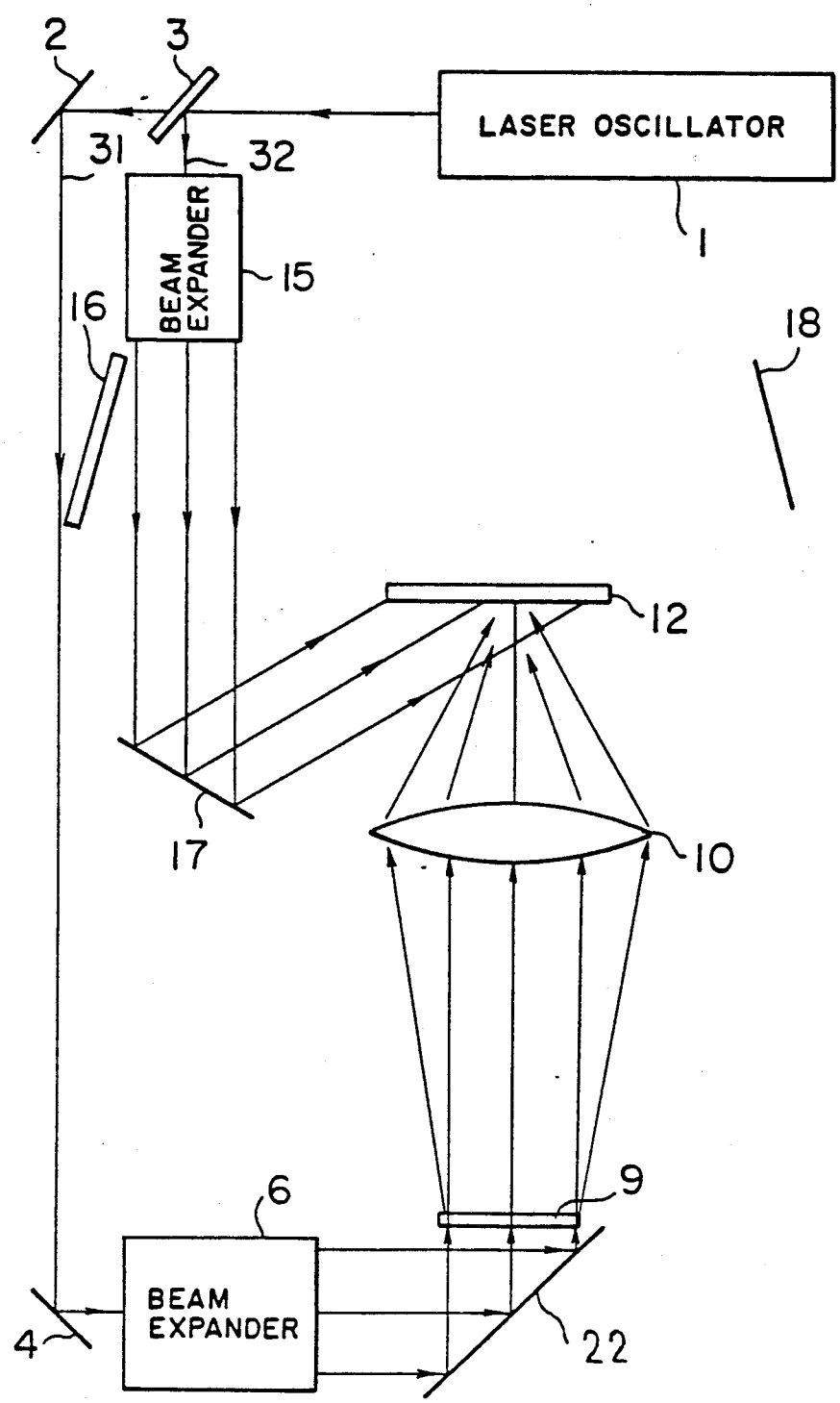

FIG. 7 shows the optical configuration of still another embodiment according to this invention in the exposure process, by which the specimen (semiconductor wafer) 9 is illuminated from below by the subject beam 31 expanded by the beam expander 6 and reflected by the reflection mirror 22. In addition, the reference beam 32 expanded by the beam expander 15 and reflected by the reflection mirror 17 illuminates the photographic plate 12 in the forward direction. Thus, a spatial frequency pattern of the defects is recorded on the photographic plate in a manner similar to the above. The photographic plate 12 is then developed and positioned again at the original position to serve as the hologram of the defects of the pattern on the specimen (semiconductor wafer) 9. In the inspection process, the reflection mirror 16 is positioned obliquely across the optical path of the expanded beam of the beam expander 15, such that the regeneration beam 33 (not shown) expanded by the beam expander 15 and reflected by the reflection mirror 16 and reflection mirror 18 illuminates the photographic plate 12 in the reverse direction. Further, the specimen (semiconductor wafer) 9 and the reflection mirror 22 are removed and an optical detector (not shown) is positioned at the position at which the specimen 9 had been positioned in the exposure process. The optical detector thus detects the defects of the pattern from the hologram of the defects formed thereat.

What is claimed is:

1. A pattern defect inspection device for detecting a defect in a periodic pattern on a surface of an object comprising:

a coherent light source for emitting a coherent light beam;

a beam splitter for dividing the coherent light beam into a subject beam and a reference beam, the subject and reference beams having respective intensities;

first optical path means for directing the subject beam onto the surface of an object having a periodic pattern thereon;

a collecting lens having front and rear focal planes for collecting light diffracted by said surface of said object;

a photographic plate having first and second sides and positioned with said collecting lens at the first side and between said object and said photographic plate, said photographic plate being disposed at the rear focal plane of said lens;

second optical path means for guiding the reference beam to the first side of said photographic plate and for adjusting the intensity of the reference beam at said photographic plate so that the reference beam interferes with light diffracted by a defect of said periodic pattern, whereby a hologram of said defect is recorded on said photographic plate;

third optical path means for guiding a coherent regeneration light beam generated by said coherent light source to said second side of said photographic plate, said photographic plate serving as a hologram, whereby a holographic image of said defect in said periodic pattern is formed by the regeneration light beam passing through said photographic plate and said collecting lens; and an optical detector for detecting said defect in said periodic pattern from the holographic image.

2. The pattern defect inspection device as claimed in claim 1 wherein said first optical path means guides the subject beam for oblique incidence on said surface of said object.

3. The pattern defect inspection device as claimed in claim 1 wherein said first optical path means guides the subject beam to said surface of said object at a right angle to said surface.

4. The pattern defect inspection device as claimed in claim 3 wherein said first optical path means guides the subject beam to said surface of said object through a side of said object opposite the side of the object on which said collecting lens is positioned.

5. The pattern defect inspection device as claimed in claim 1 wherein said second optical path means has an adjustable length for adjusting the intensity of the reference beam to interfere only with light scattered from said defect and collected by said collecting lens.

* * * * *